United States Patent [19]

Umezawa et al.

[11] Patent Number: 4,479,943
[45] Date of Patent: Oct. 30, 1984

[54] 3-DEMETHOXYISTAMYCIN B, THE 2''-N-FORMIMIDOYL DERIVATIVE THEREOF AND PHARMACEUTICAL COMPOSITION CONTAINING SAME

[75] Inventors: Hamao Umezawa, Tokyo; Shinichi Kondo, Yokohama; Daishiro Ikeda, Tokyo, all of Japan

[73] Assignee: Zaidan Hojin Biseibutsu Kagaku Kenkyu Kai, Tokyo, Japan

[21] Appl. No.: 545,686

[22] Filed: Oct. 26, 1983

[30] Foreign Application Priority Data

Nov. 5, 1982 [JP] Japan .................................. 57-193436

[51] Int. Cl.$^3$ ...................... A61K 31/71; C07H 15/22
[52] U.S. Cl. .................................. 424/180; 536/16.1; 536/16.8; 536/18.1
[58] Field of Search ............... 424/180, 181; 536/16.8, 536/18.1, 16.1

[56] References Cited

U.S. PATENT DOCUMENTS 4,232,147 11/1980 Tadanier et al. .................... 536/16.1
4,382,926 5/1983 Umezawa et al. ................. 536/16.1
4,406,891 9/1983 Umezawa et al. ................. 536/16.1

*Primary Examiner*—Johnnie R. Brown
*Attorney, Agent, or Firm*—Larson and Taylor

[57] ABSTRACT

As new compounds are provided 3-demethoxyistamycin B and 3-demethoxy-2''-N-formimidoylistamycin B which each is useful as antibacterial agent because of its high antibacterial activity against a wide variety of gram-positive and gram-negative bacteria including mycobacteria. These new compounds may be produced by removal of the 3-hydroxyl group of an N,O-protected 3-O-demethylistamycin $B_o$, followed by glycylation of the liberated 4-methylamino group and, further, if necessary, followed by formimidoylation of the 2''-amino group of an intermediate N-protected 3-demethoxyistamycin B derivative.

12 Claims, No Drawings

3-DEMETHOXYISTAMYCIN B, THE 2″-N-FORMIMIDOYL DERIVATIVE THEREOF AND PHARMACEUTICAL COMPOSITION CONTAINING SAME

SUMMARY OF THE INVENTION

This invention relates to new derivatives of istamycin B, more particularly 3-demethoxyistamycin B and 3-demethoxy-2″-N-formimidoylistamycin B which each is a useful new compound as semi-synthetic aminoglycosidic antibiotics. This invention also relates to their production and uses.

BACKGROUND OF THE INVENTION

We previously discovered new aminoglycosidic antibiotics, istamycin A, istamycin B, istamycin $A_o$ and istamycin $B_o$ which are produced by *Streptomyces tenjimariensis* SS-939, a new strain of actinomycetes, deposited in the Japanese depository "Fermentation Research Institute" under the deposit number FERM P-4932 and also in American Type Culture Collection, U.S.A. under the deposit number ATCC 31603 (see Japanese patent application pre-publication "Kokai" No. 145697/80 and No. 43295/81; U.S. Pat. No. 4,296,106; published U.K. patent application GB 2048855A). Then, we synthesized 2″-N-formimidoyl derivatives of istamycins A and B (see published U.K. patent application GB No. 2088851; U.S. Pat. No. 4,382,926 issued May 10, 1983).

Subsequently, we totally synthetized di-$N^{6'}$,$O^3$-demethylistamycin A and found its antibacterial activity against *Pseudomonas aeruginosa* to be significantly higher than the parent istamycin A (see Japanese patent application pre-publication "Kokai" No. 138180/81; U.S. patent application Ser. No. 241,649; published U.K. patent application GB No. 2073182A). We then continued our studies on istamycin antibiotics with the intention of converting istamycin B (which has a higher antibacterial activity than istamycin A) into the 3-O-demethyl derivative thereof, and we succeeded in synthetizing 3-O-demethylistamycin B and 3-O-demethyl-2″-N-formimidoylistamycin B and have found that these 3-O-demethyl derivatives of istamycin B are active not only against *Pseudomonas aeruginosa* but also against a variety of resistant bacteria (see the "Journal of Antibiotics" 33, pp. 1577–1580 (December 1980); Japanese patent application pre-publication "Kokai" No. 50996/82; U.S. patent application Ser. No. 298,844; European patent application pre-publication No. 0048549A).

At this time, we have now succeeded in synthetizing new compounds, 3-demethoxyistamycin B and 3-demethoxy-2″-N-formimidoylistamycin B represented by the general formula (I)

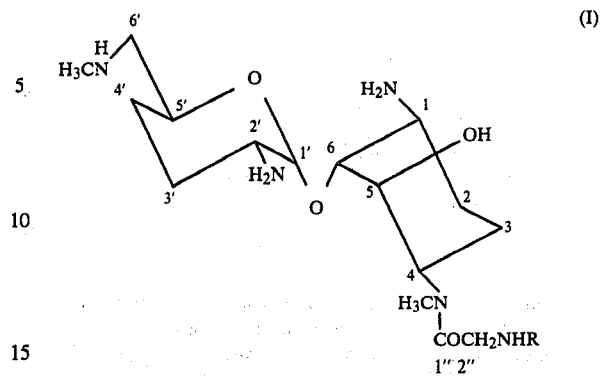

wherein R denotes a hydrogen atom for 3-demethoxyistamycin B and R denotes a formimidoyl group for 3-demethoxy-B 2″-N-formimidoylistamycin B, with employing as the starting material 3-O-demethylistamycin $B_o$ of the formula (II)

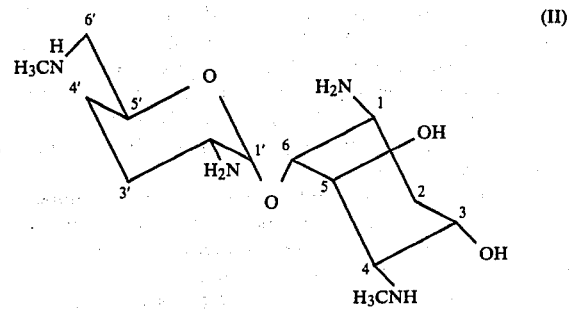

which was formed as an intermediate product in the synthesis of the above-mentioned 3-O-demethyl derivatives of istamycin B (see the Japanese patent application pre-publication "Kokai" No. 50996/82; U.S. patent application Ser. No. 298,844, filed Sept. 3, 1981; European patent application pre-publication No. 0 048549A). We have now found that the new 3-demethoxy derivatives of istamycin B now synthetized by us strongly inhibit not only the growth of *Pseudomonas aeruginosa* but also the growth of gram-negative and gram-positive bacteria, including a wide variety of gram-negative and gram-positive bacterial strains which are resistant to known aminoglycosidic antibiotics. Thus, we have accomplished this invention.

In Japanese patent application pre-publication No. 164197/81 of Watanabe et al as the inventors (ensued from Japanese patent application No. 67084/80 filed May 22, 1980), there are disclosed a 5-demethoxy derivative of each of KA-6606I, KA-6606II, and KA-6606VI [the sporaricins, see "Journal of Antibiotics", 32, 187 (1979)]; and a 5-demethoxy-4-N-glycyl derivative of KA-6606VI; as well as a 5-demethoxy derivative of each of KA-7038I and KA-7038II [the sannamycins, see "Journal of Antibiotics", 30, 1066 (1979)]. These 5-demethoxy derivatives of the sporaricins and sannamycins are generically represented by the general formula

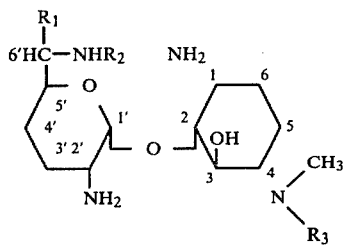

wherein $R_1$ and $R_2$ may be the same or different and each is a hydrogen atom or a methyl group, and $R_3$ is a hydrogen atom or an acyl group such as glycyl. The specification of the above Japanese patent application pre-publication "Kokai" No. 164197/81 contains at all no reference to istamycin B from which the new compounds of this invention are structurally derived. 3-Demethoxyistamycin B, one of the new compounds of this invention is clearly distinctive from the 5-demethoxy derivatives of sannamycins and sporaricins exemplified in the above-mentioned Japanese patent pre-publication "Kokai" No. 164197/81 in that the stereo configuration of the amino group at the 1-position of 3-demethoxyistamycin B and the nature of the substituent at the 6'-position of the 3-O-demethylistamycin B according to the general formula (I) are different from those of the 5-methoxy derivatives of the sannamycins and sporaricins, respectively, as this will be discussed later in more detail.

Further, in Japanese patent application pre-publication No. 7493/82 of Watanabe et al as the inventors (ensued from Japanese patent application No. 80842/80 filed June 17, 1980), there are disclosed 4-N-(N-formimidoylglycyl)derivative; 4-N-(N-formimidoyl-glycyl)-5-demethoxy derivative; and 4-N-(N-amidinoglycyl)-5-demethoxy-derivative of KA-6606II, as well as other analogues thereof which are generically represented by the general formula

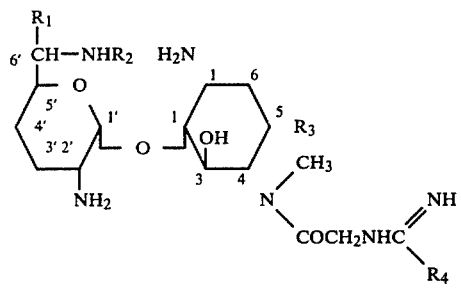

wherein $R_1$ and $R_2$ are the same or different and each is a hydrogen atom or a methyl group, $R_3$ is a hydrogen atom, a hydroxyl group or a methoxy group, and $R_4$ is a hydrogen atom or an amino group. The specification of this Japanese patent application pre-publication No. 7493/82 contains no reference to istamycin B at all, too. For the same reason as above, 3-demethoxy-2''-N-formimidoylistamycin B, the second new compound of this invention is distinguished from the known formimidoyl derivatives of a sporaricin (KA-6606II) which are exemplified in the above Japanese patent application pre-publication "Kokai" No. 7493/82, as this is discussed later in more detail.

Furthermore, we are aware of U.S. Pat. No. 4,353,893 of Watanabe et al (claiming the Convention priorities from both the aforesaid Japanese patent applications Nos. 67084/80 and 80842/80) which discloses the 5-demethoxy derivatives of some sporaricins and some sannamycins mentioned therein with regard to the aforesaid two Japanese patent application pre-publications and claims those of the formula

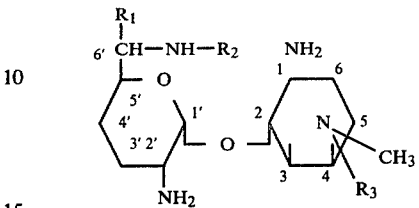

wherein $R_1$ and $R_2$ are different and each represents a hydrogen atom or a methyl group, $R_3$ represents a hydrogen atom, or a group represented by the formula -COCH$_2$NHR' in which R' is a member selected from the group consisting of a hydrogen atom, -CH=NH and $$-\underset{\underset{NH}{\|}}{C}NH_2,$$

and the symbol 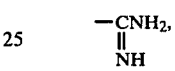 between the carbon atoms at the 5- and 6-positions represents a single or double bond.

Although the aminocyclitol rings are numbered in the opposite directions in U.S. Pat. No. 4,353,893 (as well in said two Japanese patent application pre-publications) and in the compounds disclosed and claimed therein (that is, compounds named 3-demethoxy derivatives herein are named as 5-demethoxy derivatives therein), it may be seen that the claims of U.S. Pat. No. 4,353,893 literally include within their scope the two compounds disclosed and claimed herein, i.e. 3-demethoxyistamycin B and 3-demethoxy-2''-N-formimidoylistamycin B of this invention. However, U.S. Pat. No. 4,353,893 does not exemplify either of these two compounds of this invention and, further neither discloses the starting material for the preparation of the 3-demethoxyistamycin B compounds of this invention, nor teaches how the necessary starting material may be prepared. Thus, the necessary starting material, 3-O-demethylistamycin $B_o$ used herein, and the 3-demethoxyistamycin B compounds produced herein are containing a 5'-methylaminomethyl group (—CH$_2$NHCH$_3$) and a C-1 amino group which is present in the equatorial position in the aminocyclitol moiety and in the particular stereo configuration cis to the sugar moiety, and evidently the 3-O-demethylistamycin $B_o$ required as the starting material must contain the same groups and configurations, with bearing in mind that the necessary deoxygenation, namely removal of the hydroxyl group takes place only at the 3-position of the istamycin $B_o$ compound. On the other hand, U.S. Pat. No. 4,353,893 discloses as the starting materials only such 5-O-demethyl KA-6606 compounds (the 5-O-demethyl sporaricins) which contain a C-1 amino group that is present in the equatorial position in the aminocyclitol moiety and is cis to the sugar moiety, but of which all have a 5'-(α-amino)ethyl group (—CH(NH$_2$)CH$_3$); and such 5-O-demethyl KA-7038 compounds (the 5-O-demethyl sannamycins) some of which contain a 5'-methylaminomethyl group (—CH$_2$NHCH$_3$), but of which all the sannamycin derivatives have a C-1 amino group which is trans to the sugar moiety. For these reasons, the 5-O-demethyl sporaricins and 5-O-demethyl sannamycins starting materials disclosed in U.S. Pat. No. 4,353,893 (as well as said Japanese patent application pre-publication Nos. 164197/81 and 7493/82) are, in fact, not suitable as the starting material to be employed in the production of any of the new two compounds of this invention disclosed and claimed herein, because they have the wrong 5'-substitution and/or the wrong stereo configuration of the 1-amino group. Besides, the 5-O-demethylsporaricins and 5-O-demethylsannamycins starting material disclosed in said U.S. patent are derived from the sporaricins and sannamycins which are all fermentatively produced, and they are not the chemically synthetic products, and hence said U.S. patent had no disclosure of how to obtain the necessary starting materials for the production of the new compounds disclosed and claimed herein. Thus, U.S. Pat. No. 4,353,893 as well as the aforesaid Japanese patent application pre-publications "Kokai" Nos. 164197/81 and 7493/82 do not have an enabling disclosure for the production of the necessary starting 3-O-demethylistamycin $B_0$ and the herein claimed 3-demethoxyistamycin B or 3-demethoxy-2"-N-formimidoylistamycin B of this invention.

In order to depict more clearly the differences in the steric structure and in the various substituents between the herein claimed new compounds of this invention and the prior art compounds of the above acknowledged publications, it will be worth to show that the 3-demethoxy derivatives of KA-6606 I (sporaricin A) and KA-7038 I (sannamycin A) as well as 3-demethoxyistamycin B of this invention have the following structures (see the "Journal of Antibiotics" 32, 173–179 (March 1979) and 32, 1066–1068 (October 1979); and the "Aminoglycoside Antibiotics" page 26, edited by H. Umezawa and I. R. Hooper, published from Springer-Verlag, 1982):

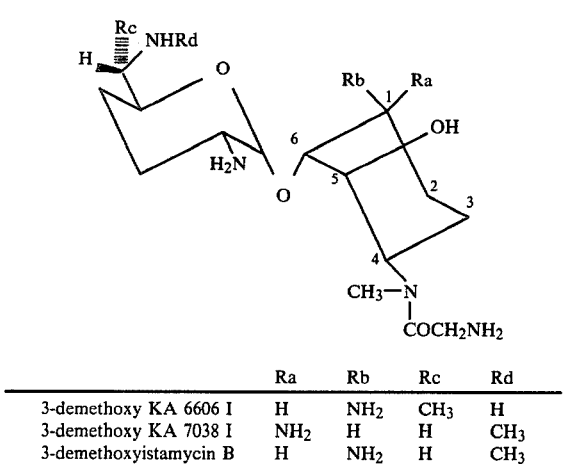

| | Ra | Rb | Rc | Rd |
|---|---|---|---|---|
| 3-demethoxy KA 6606 I | H | $NH_2$ | $CH_3$ | H |
| 3-demethoxy KA 7038 I | $NH_2$ | H | H | $CH_3$ |
| 3-demethoxyistamycin B | H | $NH_2$ | H | $CH_3$ |

Accordingly, when the stereo structures of the herein claimed two new compounds of this invention are investigated fully and compared to those of the prior art compounds, it is evident that the herein claimed new compounds are differentiated from the prior art compounds, even if the above acknowledged publications show the general formulae which literally includes the herein claimed new two compounds of this invention.

The 3-demethoxyistamycin B and 3-demethoxy-2"-N-formimidoylistamycin B described and claimed herein have been disclosed by us in the Journal of Antibiotics, 36, pp. 331–334 (March 1983), along with details of their preparation and their antibacterial activity.

DETAILED DESCRIPTION OF THE INVENTION

According to a first aspect of this invention, therefore, there is provided as a new compound 3-demethoxyistamycin B or 3-demethoxy-2"-N-formimidoylistamycin B represented by the general formula (I)

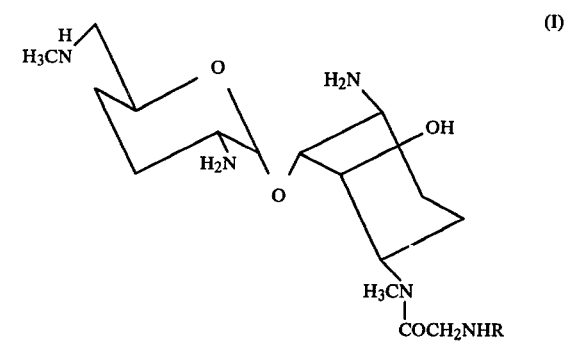

wherein R denotes a hydrogen atom for 3-demethoxyistamycin B, and R denotes a formimidoyl group (HN=CH—) for 3-demethoxy-2"-N-formimidoylistamycin B; or a pharmaceutically acceptable acid addition salt thereof.

The new compounds of the general formula (I) according to this invention have the following physico-chemical and biological properties:

(a) 3-Demethoxyistamycin B dihydrate is in the form of a hygroscopic, colorless powder which has no definite melting point but decomposes at 88°–92° C. and gives a specific optical rotation $[\alpha]_D^{24}+147°$ (c 0.35, water). Its elemental analysis gave found values: C 49.02%, H 9.85%, N 17.41% which were coincident with the theoretical value of $C_{16}H_{33}N_5O_4.2H_2O$ (C 48.59%, H 9.43%, N 17.71%).

Its thin layer chromatography on silica gel gives a single spot (positive to ninhidrin) at Rf 0.27 when developed with a lower layer of a mixture of chloroform, methanol and concentrated ammonia (2:1:1).

(b) 3-Demethoxy-2"-N-formimidoylistamycin B disulfate tetrahydrate is in the form of a colorless powder which has no definite melting point but decomposes at 201°–220° C. and gave a specific optical rotation $[\alpha]_D^{24}+89°$ (c 0.5, water). Its elemental analysis gave found values: C 31.22%, H 6.70%, N 12.13%, S 9.90% which were coincident with the theoretical value of $C_{17}H_{34}N_6O_4.2H_2O$; $4H_2O$ (C 31.19%, H 7.08%, N 12.83%, S 9.79%).

Its thin layer chromatography on silica gel gives a single spot (positive to ninhydrin) at Rf 0.31 when developed with a solution of citric acid (2.5 g) and sodium citrate (10 g) in water (50 ml).

Antibacterial spectra of 3-demethoxyistamycin B dihydrate (abbreviated as DB) and 3-demethoxy-2"-N-formimidoylistamycin B disulfate tetrahydrate (abbreviated as FDB) according to this invention are shown in Table 1 below, where the minimum inhibitory concentrations (MIC.) (mcg/ml) of these new compounds to various microorganisms are set out as calculated in term of the quantity of the free base. For comparison purpose, the MIC. values of the parent istamycin B (abbreviated as B) as well as of 3-O-demethylistamycin B (abbreviated as Demethylista B) and 3-O-demethyl-2''-formimidoylistamycin B (abbreviated as Demethylformimidoylista B) are also set out in Table 1. The results of Table 1 reveal that both the new compounds of this invention are superior in their antibacterial activity to the parent istamycin B, 3-O-demethylistamycin B and 3-O-demethyl-2''-N-formimidoylistamycin B.

of Table 1 reveal that the new compounds of the formula (I) according to this invention advantageously exhibit usefully high antibacterial activities against a wide variety of gram-negative and gram-positive bacteria. Among these istamycin derivatives, 3-demethoxyistamycin B is the most active compound.

For estimation of acute toxicity of the new compounds of this invention, their acute toxicity was tested by intravenous administration of 3-demethoxyistamycin B or 3-demethoxy-2''-N-formimidoylistamycin B in the form of their sulfate in mice and observing the mice so

TABLE 1

| | MIC. (mcg/ml) | | | | |
|---|---|---|---|---|---|
| Test microorganisms | DB | DBF | B (comparative) | Demethyl ista B (comparative) | Demethyl formimidoyl ista B (comparative) |
| Staphylococcus aureus FDA 209P | <0.20 | 0.39 | 0.39 | 0.39 | 0.39 |
| Staphylococcus aureus Smith | 0.20 | <0.20 | 0.39 | 0.39 | <0.20 |
| Staphylococcus aureus Ap01 | 0.39 | 0.39 | 0.78 | 0.39 | 0.39 |
| Staphylococcus epidermidis 109 | <0.20 | 0.20 | 0.39 | 0.39 | 0.20 |
| Micrococcus flavus FDA 16 | 3.13 | 0.39 | 12.5 | 3.13 | 0.39 |
| Sarcina lutea PCI 1001 | <0.20 | 0.39 | 0.39 | 0.39 | 0.39 |
| Bacillus anthracis | 0.39 | 0.39 | 0.78 | 0.78 | 0.39 |
| Bacillus subtilis PCI 219 | <0.20 | 0.20 | 0.39 | 0.39 | 0.20 |
| Bacillus subtilis NRRL B-558 | <0.20 | <0.20 | 0.39 | 0.39 | <0.20 |
| Bacillus cereus ATCC 10702 | 1.56 | 1.56 | 6.25 | 1.56 | 0.78 |
| Corynebacterium bovis 1810 | <0.20 | <0.20 | 0.39 | 0.39 | <0.20 |
| Mycobacterium smegmatis ATCC 607 | 0.39 | 0.39 | 0.78 | 0.78 | 0.39 |
| Escherichia coli NIHJ | 0.39 | 0.20 | 0.39 | 0.39 | 0.39 |
| Escherichia coli K-12 | 0.78 | 0.39 | 0.78 | 0.78 | 0.78 |
| Escherichia coli K-12 R5 | 1.56 | 0.78 | 1.56 | 3.13 | 0.78 |
| Escherichia coli K-12 R388 | 0.39 | 0.39 | 0.78 | 0.78 | 0.78 |
| Escherichia coli K-12 J5R11-2 | 0.78 | 0.78 | 1.56 | 1.56 | 1.56 |
| Escherichia coli K-12 ML1629 | 0.78 | 0.39 | 1.56 | 1.56 | 0.78 |
| Escherichia coli K-12 ML1630 | 3.13 | 1.56 | 3.13 | 3.13 | 1.56 |
| Escherichia coli K-12 ML1410 | 1.56 | 1.56 | 3.13 | 3.13 | 1.56 |
| Escherichia coli K-12 ML1410 R81 | 0.78 | 0.39 | 1.56 | 1.56 | 1.56 |
| Escherichia coli K-12 LA290 R55 | 1.56 | 0.78 | 1.56 | 0.78 | 0.78 |
| Escherichia coli K-12 LA290 R56 | 0.39 | 0.39 | 1.56 | 0.78 | 0.78 |
| Escherichia coli K-12 LA290 R64 | 0.78 | 0.78 | 1.56 | 1.56 | 1.56 |
| Escherichia coli W677 | 0.39 | 0.39 | 0.78 | 0.78 | 0.39 |
| Escherichia coli JR66/W677 | 0.78 | 0.39 | 1.56 | 1.56 | 1.56 |
| Escherichia coli K-12 C600 R135 | 0.78 | 6.25 | 12.5 | 1.56 | 6.25 |
| Escherichia coli JR225 | 0.78 | 0.39 | 1.56 | 0.78 | 0.39 |
| Klebsiella pneumoniae PCI602 | 0.78 | 0.78 | 3.13 | 1.56 | 0.78 |
| Klebsiella pneumoniae 22#3038 | 1.56 | 1.56 | 1.56 | 3.13 | 1.56 |
| Shigella dysenteriae JS11910 | 1.56 | 1.56 | 3.13 | 3.13 | 1.56 |
| Shigella flexneri 4B JS11811 | 1.56 | 1.56 | 3.13 | 3.13 | 1.56 |
| Shigella sonnei JS11746 | 1.56 | 1.56 | 1.56 | 1.56 | 1.56 |
| Salmonella typhi T-63 | <0.20 | 0.39 | 0.39 | 0.39 | <0.20 |
| Salmonella enteritidis 1891 | 1.56 | 1.56 | 3.13 | 1.56 | 1.56 |
| Proteus vulgaris OX19 | 0.39 | <0.20 | 0.39 | 0.39 | 0.39 |
| Proteus rettgeri GN311 | 0.39 | 0.39 | 0.78 | 0.39 | 0.39 |
| Proteus rettgeri GN466 | 0.39 | <0.20 | 0.78 | 0.39 | 0.39 |
| Serratia marcescens | 0.78 | 0.78 | 1.56 | 1.56 | 1.56 |
| Serratia sp. SOU | 3.13 | 12.5 | 25 | 6.25 | 12.5 |
| Serratia sp. 4 | 12.5 | 12.5 | 50 | 12.5 | 12.5 |
| Providencia sp. Pv16 | 0.78 | 0.78 | 1.56 | 0.78 | 0.78 |
| Providencia sp. 2991 | 1.56 | 1.56 | 3.13 | 1.56 | 0.78 |
| Pseudomonas aeruginosa A3 | 0.39 | 0.39 | 1.56 | 0.20 | 0.20 |
| Pseudomonas aeruginosa No. 12 | 12.5 | 25 | 50 | 12.5 | 12.5 |
| Pseudomonas aeruginosa H9 | 12.5 | 25 | 50 | 12.5 | 12.5 |
| Pseudomonas aeruginosa H11 | 25.0 | 50 | 100 | 25 | 25 |
| Pseudomonas aeruginosa TI-13 | 6.25 | 12.5 | 50 | 6.25 | 12.5 |
| Pseudomonas aeruginosa GN315 | 6.25 | 50 | 50 | 6.25 | 6.25 |
| Pseudomonas aeruginosa 99 | 25 | >100 | 100 | 25 | 100 |
| Pseudomonas aeruginosa B-13 | 50 | >100 | >100 | 25 | 100 |
| Pseudomonas aeruginosa 21-75 | 50 | 50 | 100 | 25 | 25 |
| Pseudomonas aeruginosa PST1 | 12.5 | 25 | 50 | 12.5 | 25 |
| Pseudomonas aeruginosa ROS 134/PU21 | 50 | 100 | >100 | 50 | 100 |
| Pseudomonas aeruginosa K-Ps 102 | 12.5 | 25 | 50 | 6.25 | 12.5 |
| Pseudomonas maltophilia GN 907 | 100 | >100 | 100 | 100 | >100 |

The minimum inhibitory concentrations indicated in Table 1 above have been determined according to a standard serial dilution method on nutrient agar plates which were incubated at 37° C. for 17 hours. The results treated during the consecutive 14 days, when it was found that all the treated mice tolerated dose of 100 mg/kg (calculated in term of the free base) of each compound, revealing that the new compounds of this invention each is of a low toxicity.

3-Demethoxyistamycin B or 3-methoxy-2''-N-formimidoylistamycin B according to this invention may be obtained in the form of the free base, a hydrate or a carbonate thereof. More preferably, in view of their stability, they can be converted into a pharmaceutically acceptable acid addition salt thereof by reacting with a pharmaceutically acceptable acid in a usual manner. Examples of the pharmaceutically acceptable acids are inorganic acids such as hydrochloric, hydrobromic, sulfuric, phosphoric and nitric acids and organic acids such as acetic, malic, citric, ascorbic and methanesulfonic acids.

The production of 3-demethoxyistamycin B represented by the formula (Ia)

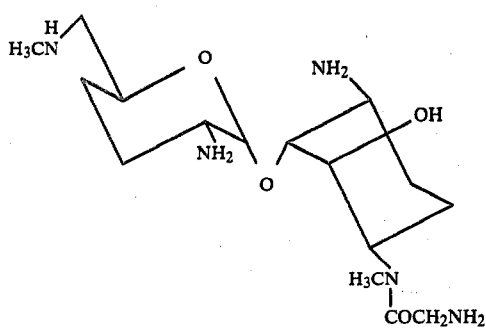

can principally be achieved by using 3-O-demethylistamycin $B_o$ of the formula (II):

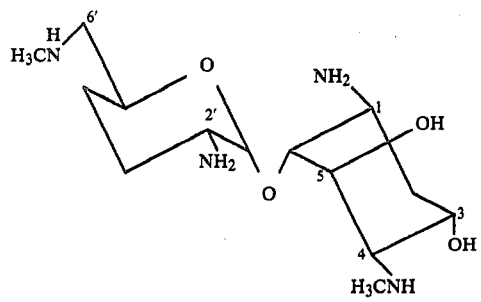

(see the aforesaid Japanese patent application pre-publication "Kokai" No. 50996/82; U.S. Pat. No. 4,296,106) as the starting compound, protecting preferentially the 1- and 2'-amino groups as well as the 6'-methylamino group of 3-O-demethylistamycin $B_o$ with known amino-protecting groups, respectively, then protecting simultaneously the 4-methylamino group and the 5-hydroxyl group of the 1,2',6'-tri-N-protected 3-O-demethylistamycin $B_o$ obtained (the 4-methylamino group being present in the cis-position relative to the 5-hydroxyl group and trans-position relative to the 3-hydroxyl group in the 3-O-demethylistamycin $B_o$ molecule) so as to give such an N,O-protected 3-O-demethylistamycin $B_o$ derivative, of which all the 1- and 2'-amino groups, the 4-methylamino groups and the 5-hydroxyl group other than the 3-hydroxyl group have been protected, thereafter removing therefrom the 3-hydroxyl group (i.e. for the 3-deoxygenation), removing the protecting group for the simultaneous protection of the 4-methylamino and 5-hydroxyl groups to produce such a 1,2',6'-tri-N-protected 3-demethoxyistamycin $B_o$ derivative of the formula (III)

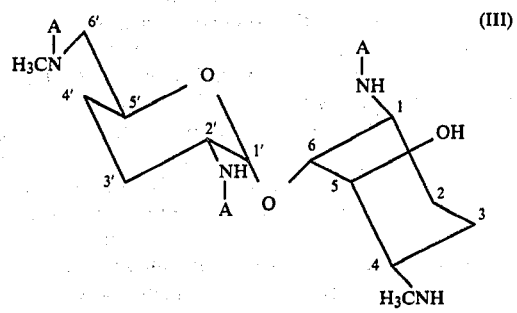

wherein A denotes a mono-valent amino-protecting group, then acylating the 4-methylamino group of the compound of the formula (III) with glycine or an N-protected derivative of glycine represented by the formula (IV)

HOOCCH$_2$NHB            (IV)

wherein B denotes a hydrogen atom or an amino-protecting group, to produce such a 1,2',6'-tri-N-protected or 1,2',6',2''-tetra-N-protected 3-demethoxyistamycin B derivative of the formula (V)

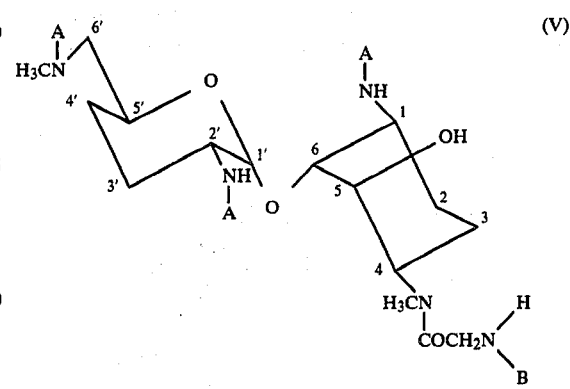

wherein A and B each denotes the amino-protecting group as defined above, and finally removing all the amino-protecting groups (A,B) from the compound of the formula (V) to give the desired 3-demethoxyistamycin B.

Preferred procedures for carrying out the production of 3-demethoxyistamycin B according to this invention are now described.

In the first step, the 1- and 2'-amino groups and the 6'-methylamino group of 3-O-demethylistamycin $B_o$ of the formula (II) are protected simultaneously with mono-valent amino-protecting groups (A), respectively, without affecting the 4-methylamino group thereof. As such a mono-valent amino-protecting group available for that purpose, there may be mentioned an alkoxycarbonyl group, particularly having 2–7 carbon atoms, such as tert-butoxycarbonyl and tert-amyloxycarbonyl; a cycloalkyloxycarbonyl group, particularly of 4–7 carbon atoms such as cyclohexyloxycarbonyl; an aralkyloxycarbonyl group such as benzyloxycarbonyl; and an acyl group, particularly an alkanoyl group having 2–7 carbon atoms such as trifluoroacetyl and o-nitrophenoxyacetyl. The introduction of such an amino-protecting group may be carried out in a manner known in the syntheses of peptides, e.g. by using a known amino-protecting group-introducing reagent in the form of an acid halide, an acid azide, an active ester, an acid anhydride, etc. By using such an amino-protecting group-introducing reagent in an amount of 2.5-3.5 moles per mole of 3-O-demethylistamycin $B_o$, it is possible to preferentially form a 1,2',6'-tri-N-protected 3-O-demethylistamycin $B_o$ derivative, due to the difference in reactivity of the respective amino and methylamino groups of 3-O-demethylistamycin $B_o$. Preferably, such 1,2',6'-tri-N-protected 3-O-demethylistamycin $B_o$ may be obtained in a higher yield by reacting 3-O-demethylistamycin $B_o$ with 1-3 molar equivalents of a divalent cation such as those of divalent transition metals such as copper, nickel and cobalt and of zinc (II) to form a metal complex, and reacting the complex with 3-5 moles of an amino-protecting group-introducing reagent, followed by removal of the metal cation from the reaction product (see U.S. Pat. No. 4,297,485).

In the molecule of the istamycin B or $B_o$ compound, the adjacent 4-methylamino and 5-hydroxyl groups are positioning in the cis-relationship with each other. For the purpose of simultaneously protecting both the 4-methylamino and 5-hydroxyl groups, it is most convenient to adopt the technique that these methylamino and hydroxyl groups are protected by conversion of them into the form of a cyclic carbamate. In the second step, therefore, the 1,2',6'-tri-N-protected 3-O-demethylistamycin $B_o$ derivative obtained from the first step is converted into its cyclic 4,5-carbamate derivative of the formula (IV)

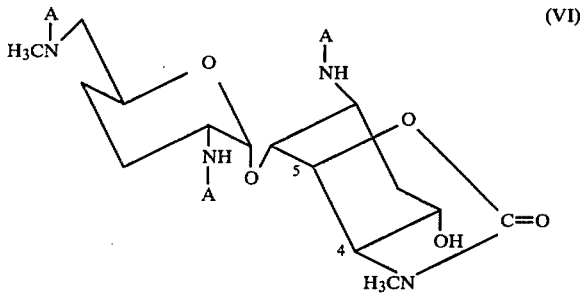

wherein A denotes a mono-valent amino-protecting group, for example, by reacting the 1,2',6'-tri-N-protected 3-O-demethylistamycin $B_o$ derivative with an equimolar or substantially equimolar proportion of N,N'-carbonyldiimidazole

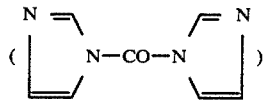

in an anhydrous organic solvent, such as dry toluene at a temperature of 50°-100° C., or alternatively by reacting the 1,2',6'-tri-N-protected 3-O-demethylistamycin $B_o$ derivative with an alkyl- or aryl (or aralkyl)-chloroformate, particularly benzylchloroformate to produce a corresponding 4-N-alkyloxycarbonylated or 4-N-aryl (or aralkyl)oxycarbonylated derivative, followed by treating the latter with a basic reagent such as sodium hydride and the like in an anhydrous organic solvent such as dry dimethylformamide at a temperature of 0° C. or below (see published U.K. patent application GB No. 2073182 A).

In the third step, the deoxygenation of the 3-hydroxyl group (namely, the removal of the 3-hydroxyl group) is effected in the 1,2',6'-tri-N-protected 3-O-demethylistamycin $B_o$ 4,5-carbamate derivative of the formula (VI) which was obtained from the second step as above. This 3-deoxygenation can be accomplished according to any of conventional methods which have usually been employed in the production of known deoxy derivatives of aminoglycosidic antibiotics. For instance, the 3-hydroxyl group is alkylsulfonylated, arylsulfonylated or aralkylsulfonylated by reacting with an alkylsulfonyl, arylsulfonyl or aralkylsulfonyl chloride or a reactive equivalent thereof in an anhydrous organic solvent such as pyridine to produce a corresponding 3-O-alkylsulfonyl, 3-O-arylsulfonyl or 3-O-aralkylsulfonyl derivative of the 1,2',6'-tri-N-protected 3-O-demethylistamycin $B_o$ 4,5-carbamate compound, and then the 3-O-alkylsulfonyl, 3-O-arylsulfonyl or 3-O-aralkylsulfonyl derivative so produced is reacted with a sodium halide such as sodium chloride or iodide to produce a corresponding 3-halo derivative which is subsequently reduced by catalytic reduction with hydrogen or reduction with a metal hydride such as tributylstannane to replace the 3-halo group by a hydrogen atom. In this way, the 3-deoxygenation can be achieved in a facile manner. As an alternative and more preferred method, direct conversion of the 3-hydroxyl group into the 3-chloro group can be achieved by reacting the 1,2',6'-tri-N-protected 3-O-demethylistamycin $B_o$ 4,5-carbamate compound with an equimolar or substantially equimolar proportion of sulfuryl chloride in dry pyridine, and then the resulting 3-chloro derivative is catalytically reduced with hydrogen or reduced with a metal hydride to effect the dechlorination and thereby give the 3-deoxy derivative. For the latter method, tributylstannane or other trialkyltin hydride or the like may preferably be employed as the metal hydride in the dechlorination stage thereof. Thus, the third step affords the 1,2',6'-tri-N-protected 3-demethoxyistamycin $B_o$ 4,5-carbamate derivative of the formula (VII)

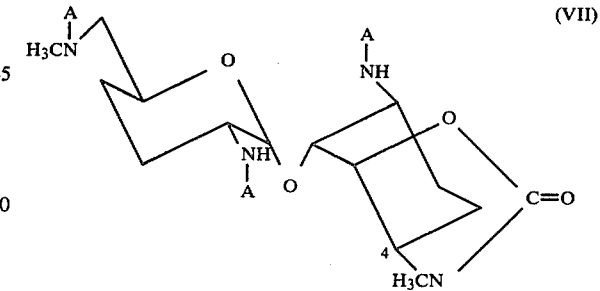

wherein A denotes the amino-protecting group as defined above.

In the fourth step, the cyclic 4,5-carbamate group is removed from the carbamate compound of the formula (VII). To this end, the removal of the cyclic 4,5-carbamate group can easily be achieved by hydrolysis under alkaline conditions using e.g. aqueous barium hydroxide or 0.1M aqueous sodium hydroxide at 40°-120° C. in a known manner. In this way, there is obtained the 1,2',6'-tri-N-protected 3-demethoxyistamycin $B_o$ derivative of the formula (III) shown hereinbefore which forms an important, key intermediate for this invention.

In the fifth step, the 4-methylamino group of the intermediate 1,2',6'-tri-N-protected compound of the formula (III) is glycylated (i.e. acylated with glycine). The glycylation of the 4-methylamino group of the 1,2′,6′-tri-N-protected 3-demethoxyistamycin $B_o$ compound (III) may be effected by reacting the compound (III) with glycine or a reactive derivative thereof in accordance with any of known N-acylation processes for peptide-synthesis such as the dicyclohexylcarbodiimide process, mixed acid anhydride process, azide process, active ester process, etc. It is preferable for the glycine reagent to have its amino group protected, and the amino-protecting group for this purpose may be the same as or different from those on the 1- and 2′-amino groups and on the 6′-methylamino group of the starting 3-O-demethylistamycin $B_o$ and may preferably be such one which is easily removable. Thus, the amino-protecting group for protecting the amino group in the glycine reagent may be selected from the above-mentioned amino-protecting groups and some divalent amino-protecting groups such as ones of a Schiff base type. The glycylation reaction is preferably carried out according to an active ester process in an organic solvent such as dioxane under heating to a temperature of 40°–60° C. In effecting the above glycylation for the production of 3-demethoxyistamycin B, however, it is convenient that the amino-protecting group employed for the protection of the amino group of the glycine reagent is such an amino-protecting group of the same nature as those which have been used for the protection of the 1- and 2′-amino groups and 6′-methylamino group of the starting 3-O-demethylistamycin $B_o$. In this fifth step, there is thus obtained the 1,2′,6′,2″-tetra-N-protected 3-demethoxyistamycin B derivative of the formula (V) shown hereinbefore.

In the sixth step, the tetra-N-protected 3-demethoxyistamycin B of the formula (V) is subjected to the deprotecting reaction for removal of all the remaining amino-protecting groups therefrom in order to produce the desired 3-demethoxyistamycin B. The removal of the amino-protecting groups on the amino and methylamino groups of the compound of the formula (V) may be effected in a known manner. For example, hydrogenolysis in the presence of palladium, platinum oxide, etc. as catalyst is effective for the removal of an aralkyloxycarbonyl group, and hydrolysis in an aqueous solution of trifluoroacetic acid, acetic acid, etc. or a diluted aqueous acid solution such as a diluted hydrochloric acid is suitable for the removal of the amino-protecting group of the other nature such as alkyloxycarbonyl group. It is advisable that the nature of the amino-protecting group employed for the glycine reagent is properly selected with taking into account the reaction conditions which are usable in the deprotection step of removing the amino-protecting groups from the respective amino groups of the compound of the formula (V).

The production of 3-demethoxy-2″-N-formimidoylistamycin B according to the general formula (I) where R denotes the groups HN=CH—, which is represented by the formula (Ib)

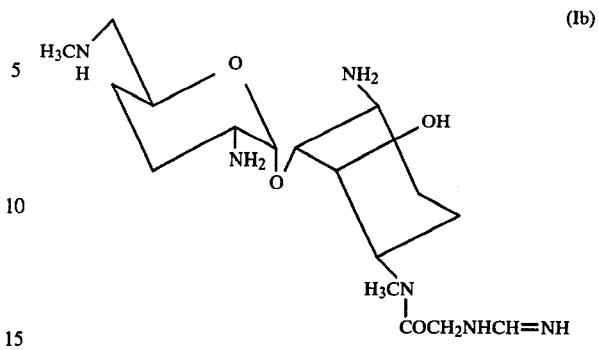

can be conducted by acylating the 4-methylamino group of a 1,2′,6′-tri-N-protected 3-demethoxyistamycin $B_o$ with glycine or an N-protected derivative of glycine represented by the formula (IV′)

$$HOOCCH_2NHB' \qquad (IV')$$

wherein B′ denotes a hydrogen atom or an amino-protecting group which is different in its nature from those of the amino-protecting groups present at the 1-, 2′- and 6′-positions of the compound of the formula (III) and must easily be cleavable preferentially by a de-protecting technique different from those de-protecting techniques applicable for the cleavage of the amino-protecting groups at the 1-, 2′- and 6′-positions of the compound (III), whereby there is formed such a 1,2′,6′-tri-N-protected or 1,2′,6′,2″-tetra-N-protected 3-demethoxyistamycin B derivative of the formula (V′)

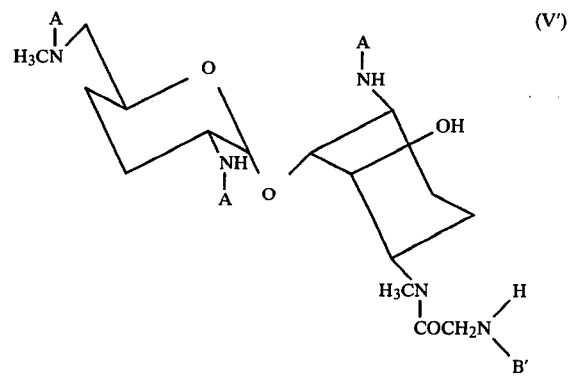

wherein A is each the amino-protecting group as defined above and B′ is the amino-protecting group of the different nature from that of A. Then, if required, the compound of the formula (V′) is subjected to the N-deprotecting reaction for preferential removal of the amino-protecting group (B′) which is present at the amino group of the glycine moiety of the compound (V′), to produce a 1,2′,6′-tri-N-protected demethoxyistamycin B of the formula (V″)

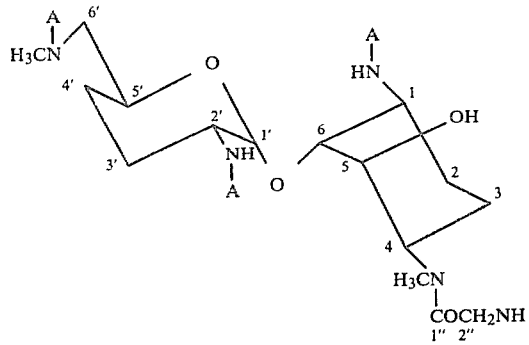
(V‴)

wherein A is the amino-protecting group as defined above.

In further steps, the compound of the formula (V‴) is formimidoylated so as to convert its 2″-amino group into an amidine group, followed by the removal of the remaining aminoprotective groups at the 1-, 2′- and 6′-positions of the 2″-N-formidoylated product to give the desired 3-demethoxy-2″-N-formimidoylistamycin B of the formula (Ib). Thus, in order to convert the 2″-amino group of the 1,2′,6′-tri-N-protected 3-demethoxyistamycin B derivative of the formula (V‴) (as obtained by the preferential cleavage of the amino-protective group at the 2″-position) into the amidine group, the compound of the formula (V‴) is formimidoylated by reacting with an iminoether reagent of the fromula (VIII)

R″OCH=NH (VIII)

wherein R″ represents a lower ($C_1$–$C_4$) alkyl group or an aralkyl group such as benzyl, or an acid addition salt thereof such as hydrochloride and sulfate. The use of an iminoether hydrochloride such as ethylformimidate hydrochloride and benzylformimidate hydrochloride is preferred. The formimidoylation reaction may be conducted in an organic solvent such as dioxane and methanol or in an aqueous solution at a temperature of below 30° C. in a known manner. The resulting 1,2′,6′-tri-N-protected-3-demethoxy-2″-N-formimidoylistamycin B, or an acid addition salt thereof may be purified by a column chromatography using a silica gel and the like, if required.

The remaining amino-protecting groups on the 1- and 2′-amino groups and on the 6′-methylamino group of the 2″-N-formimidoylated compound may be removed by a known method as above-mentioned, thus to yield the desired 3-demethoxy-2″-N-formimidoylistamycin B of formula (Ib). 3-Demethoxy-2″-N-formimidoylistamycin B so produced according to this invention may preferably be obtained in the form of its acid addition salt, especially a pharmaceutically acceptable acid addition salt, in view of its enhanced stability upon storage.

According to a second aspect of this invention, therefore, there is provided a process for the production of 3-demethoxyistamycin B, which comprises the consecutive steps of:

(a) providing a 1,2′,6′-tri-N-protected 3-O-demethylistamycin $B_o$ 4,5-carbamate derivative of the formula (VI)

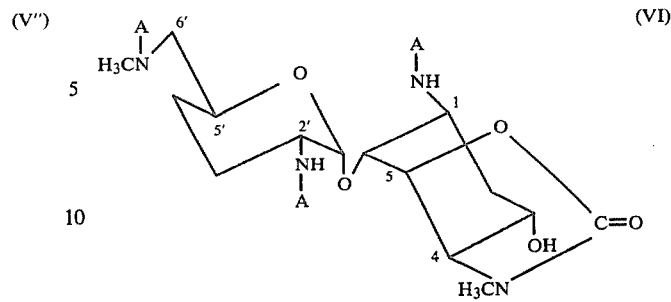
(VI)

wherein A denotes a mono-valent amino-protecting group, (b) removing the 3-hydroxyl group from the compound of the formula (VI) to produce a 1,2′,6′-tri-N-protected 3-demethoxyistamycin $B_o$ 4,5-carbamate derivative of the formula (VII)

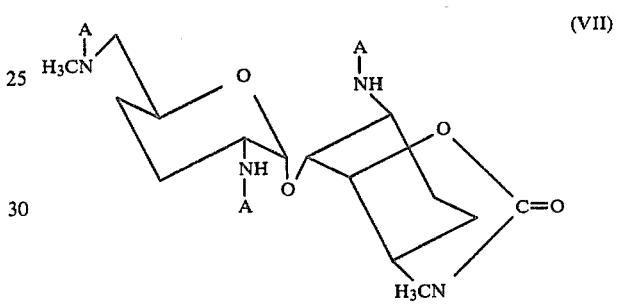
(VII)

wherein A is as defined above, (c) fissioning the cyclic 4,5-carbamate moiety of the compound of the formula (VII) by alkaline hydrolysis to produce a 1,2′,6′-tri-N-protected 3-demethoxyistamycin $B_o$ derivative of the formula (III)

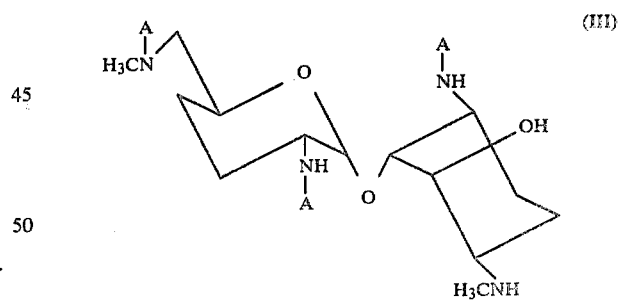
(III)

wherein A is as defined as above, (d) acylating the 4-methylamino group of the compound of the formula (III) with glycine or an N-protected glycine derivative of the formula (IV)

HOOCCH₂NHB (IV)

wherein B is a hydrogen atom or an amino-protecting group of the nature same as or different from the amino-protecting group A, or a functional equivalent of said glycine compound, to produce a 1,2′,6′-tri-N-protected or 1,2′,6′,2″-tetra-N-protected 3-demethoxyistamycin B derivative of the formula (V)

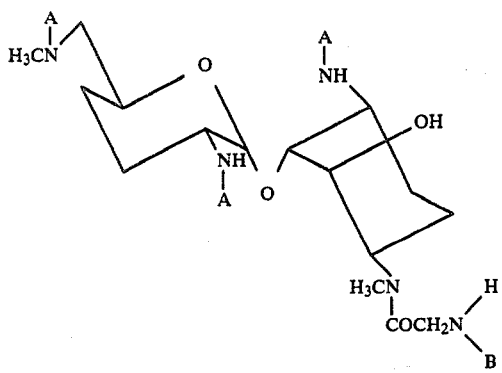

(V)

wherein A and B are as defined above, and (e) removing all the remaining amino-protecting groups (A and B) from the compound of the formula (V) to give the desired 3-demethoxyistamycin B.

According to a third aspect of this invention, there is provided a process for the production of 3-demethoxy-2''-N-formimidoylistamycin B, which comprises the consecutive steps of:

(a) providing a 1,2',6'-tri-N-protected 3-O-demethylistamycin $B_o$ 4,5-carbamate derivative of the formula (VI)

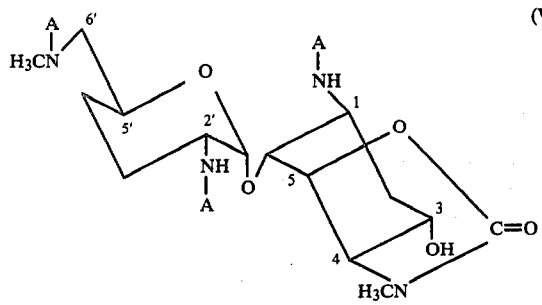

(VI)

wherein A denotes a mono-valent amino-protecting group, (b) removing the 3-hydroxyl group from the compound of the formula (VI) to produce a 1,2',6'-tri-N-protected 3-demethoxyistamycin $B_o$ 4,5-carbamate derivative of the formula (VII)

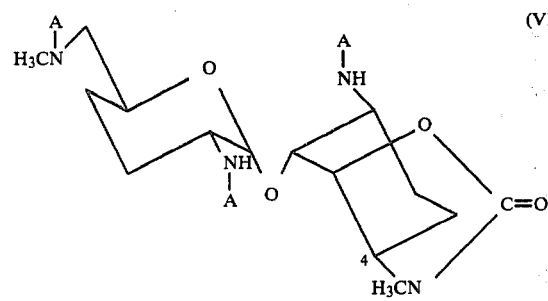

(VII)

wherein A is as defined above, (c) fissioning the cyclic 4,5-carbamate moiety of the compound of the formula (VII) by alkaline hydrolysis to produce a 1,2',6'-tri-N-protected 3-demethoxyistamycin $B_o$ derivative of the formula (III)

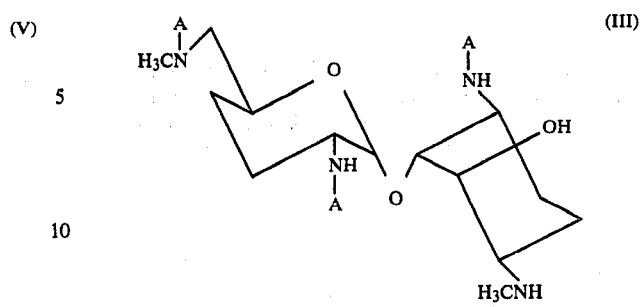

(III)

wherein A is as defined above, (d) acylating the 4-methylamino group of the compound of the formula (III) with glycine or an N-protected glycine derivative of the formula (IV')

HOOCCH$_2$NHB'   (IV')

wherein B' is a hydrogen atom or an amino-protecting group of the nature different from that of the amino-protecting group A, or a functional equivalent of said glycine compound, to produce a 1,2',6'-tri-N-protected or 1,2',6',2''-tetra-N-protected 3-demethoxyistamycin B derivative of the formula (V')

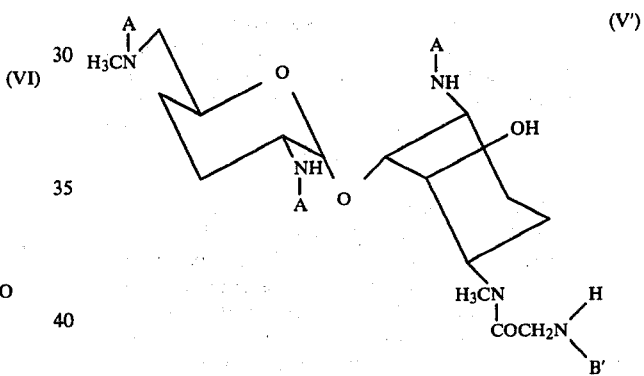

(V')

wherein A and B' are as defined above, (e) removing preferentially the amino-protecting group (B') from the 2''-amino group of the compound of the formula (V') where B' denotes the amino-protecting group, to produce the 1,2',6'-tri-N-protected 3-demethoxyistamycin B derivative of the formula (V'')

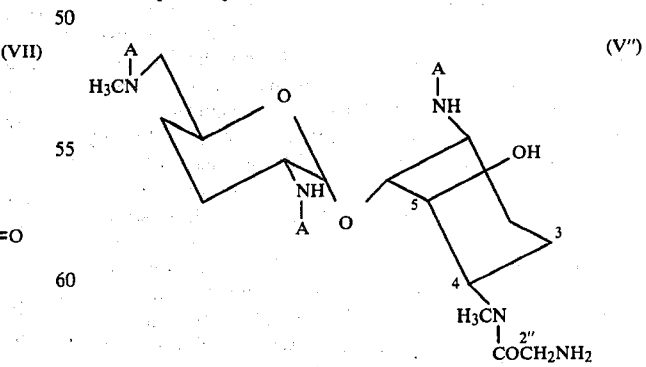

(V'')

wherein A is as defined above, (f) reacting the 2''-amino group of the compound of the formula (V'') with an iminoether of the formula (VIII)

$$R''OCH=NH \quad (VIII)$$

wherein R″ is a (C₁–C₄)alkyl group or an aralkyl group, or an acid addition salt of said iminoether to produce a 1,2′,6′-tri-N-protected 3-demethoxy-2″-N-formimidoylistamycin B derivative of the formula (Ib′)

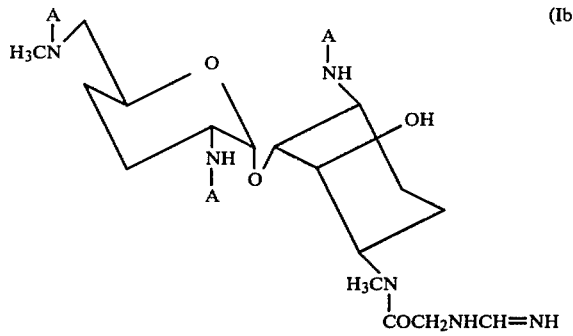

wherein A is as defined above, and (e) removing all the remaining amino-protecting groups (A) from the compound of the formula (Ib′) to give the desired 3-demethoxy-2″-N-formimidoylistamycin B.

The process according to the second or third aspect of this invention may, if desired, include a further step of reacting 3-demethoxyistamycin B or 3-demethoxy-2″-N-formimidoylistamycin B product with a pharmaceutically acceptable inorganic or organic acid to form the corresponding pharmaceutically acceptable acid addition salt thereof.

As already described, the new compound (I) of this invention possesses a high antibacterial activity against a wide variety of bacteria. Further, the compound has a low toxicity to animals as shown by the results that mice tolerated intravenous administration of 100 mg/Kg of the compound. Thus, the compound is very useful as an antibacterial agent and for this purpose it is generally formulated into the form of pharmaceutical composition, which may be administered into man or an animal in a way known per se.

Accordingly, this invention also provides a pharmaceutical composition comprising a therapeutically or bactericidally effective amount of the compound of above formula (I) or a pharmaceutically acceptable acid addition salt thereof in combination with a pharmaceutically acceptable carrier or adjuvant. This invention furhter provides a method of inhibiting the bacterial growth in an animal which comprises administering a therapeutically or bactericidally effective amount of the compound (I) or a pharmaceutically acceptable salt thereof to an animal infected with or susceptible to bacteria. It will be appreciated that an appropriate amount of the effective ingredient to be administered for the envisaged purpose will vary depending upon the particular composition formulated, the mode of administration, the conditions to be treated and the nature of the bacteria to be controlled thereby. By way of general guidance, the effective ingredient will be administered into an animal at a dosage of 0.5–10 mg per kg of the animal body.

This invention is further illustrated but not limited by the following Example.

It may be added that 3-O-demethylistamycin B_o used as the starting material in the processes of this invention may be prepared by the method described in the specification of Japanese patent application pre-publication No. 50996/82 or published European patent application pre-publication No. 0048549 A as illustrated by a Reference Example given hereinafter.

EXAMPLE 1

Synthesis of 3-demethoxyistamycin B (1) Preparation of 1,2′,6′-tri-N-tert-butoxycarbonyl-3-demethoxyistamycin $B_o$ (a) 3-O-demethylistamycin $B_o$ dicarbonate (510 mg, 1.16 milimoles) which was obtained by the procedure of Reference Example given hereinafter was dissolved in 20 ml of methanol, and the resultant solution was admixed with 680 mg (2.72 milimoles) of nickel acetate tetrahydrate [Ni(OOCCH₃)₂.4H₂O], followed by stirring at ambient temperature for 4.5 hours. To the reaction solution containing therein the complex of 3-O-demethylistamycin $B_o$ and cobalt cation so formed was added 1.34 g (5.45 milimoles) of 2-(tert-butoxycarbonyloxyimino)-2-phenylacetonitrile (BOC-ON, a product of Aldrich Co., U.S.A.) as the tert-butoxycarbonyl-introducing reagent, and the resulting mixture was stirring at ambient temperature overnight to effect the tert-butoxycarbonylation of the amino groups in said complex. The reaction solution obtained was admixed with 2 ml of conc. aqueous ammonia and then stirred for 30 minutes, followed by concentration under reduced pressure to effect the cleavage of the cobalt cations from the N-tert-butoxycarbonylated 3-O-demethylistamycin $B_o$ moiety of said complex. The residue was taken up into 40 ml of chloroform and the solution obtained was washed three times with 40 ml portions of 1N aqueous ammonia and once with water. The chloroform phase (the solution) was dehydrated over anhydrous sodium sulfate and then concentrated to dryness under reduced pressure. The residue so obtained was purified by column chromatography on silica gel (Wako Gel C-200, a product of Wako Junyaku Co., Japan, 100 g) developed with chloroform-methanol-17% aqueous ammonia (80:10:1 by volume) to afford 617 mg of a colorless powder comprising 1,2′, 6-tri-N-tert-butoxycarbonyl-3-O-demethylistamycin $B_o$. Yield 86%.

(b) 1,2′,6′-Tri-N-tert-butoxycarbonyl-3-O-demethylistamycin $B_o$ (560 mg, 0.906 milimoles) obtained by the above procedure (a) was dissolved in 10 ml of dry toluene, and to the resulting solution was added 162 mg (0.997 milimoles) of N,N′-carbonyldiimidazole, followed by heating at 60° C. for 2.5 hours to effect the reaction of the N,N′-carbonyldiimidazole with the 4-methylamino and 5-hydroxyl groups of the N-protected 3-O-methylistamycin $B_o$ compound. The reaction solution was admixed with 20 ml of toluene and then washed twice with 1N aqueous ammonia and then once with water. The washed toluene phase (the solution in toluene) was dried over anhydrous sodium sulfate and concentrated undre reduced pressure. The residue was purified by column chromatography on silica gel (Wako Gel C-2-0, 80 g) developed with ethyl acetate-toluene (10:1) to afford 472 mg of a colorless powder comprising 1,2′,6′-tri-N-tert-butoxycarbonyl-3-O-demethylistamycin $B_o$ 4,5-carbamate. Yield 81%. IR. 1755 cm⁻¹ (five-membered cyclic carbamate).

(c) 1,2′,6′-Tri-N-tert-butoxycarbonyl-3-O-demethylistamycin $B_o$ 4,5 -carbamate (352 mg, 0.547 milimoles) obtained by the above procedure (b) was dissolved in 10 ml of dry pyridine. Under argon atmosphere, the solution in pyridine was cooled to −30° C., followed by dropwise addition thereto of 0.12 ml (1.62 milimoles) of sulfuryl chloride ($SO_2Cl_2$). The reaction mixture was slowly raised to −10° C. and allowed to undergo the reaction for 3.5 hours at that temperature (to effect the replacement of the 3-hydroxyl group by a chloro group). The reaction solution was admixed with 1.0 ml of water, then stirred at 0° C. for 30 minutes and concentrated under reduced pressure. The residue was dissolved in 30 m of chloroform and the solution obtained was washed with 10% aqueous potassium hydrogen sulfate, then with saturated aqueous sodium hydrogen carbonate and finally with water. The washed chloroform phase (the solution in chloroform) was dried over anhydrous sodium sulfate and then concentrated under reduced pressure. The residue was purified by column chromatography on silica gel (Wako Gel C-200, 50 g) developed with chloroform-methanol (80:1) to give 360 mg of a colorless powder comprising 1,2′,6′-tri-N-tert-butoxycarbonyl-3-demethoxy-3-epi-chloro-istamycin $B_o$ 4,5-carbamate. Yield 99%.

(d) A colorless powder of 1,2′,6′-tri-N-tert-butoxycarbonyl-3-demethoxy-3-epi-chloro-istamycin $B_o$ 4,5-carbamate (347 mg. 0.523 milimoles) obtained in the above procedure (c) was dissolved in 12 ml of toluene, and the resulting solution was admixed with 0.6 ml of tributylstannane and a catalytic quantity of α,α-azobisisobutyronitrile. The admixture obtained was stirred at 120° C. for 3 hours under stream of argon gas to effect the reductive replacement of the 3-chloro group by a hydrogen atom. The reaction solution was passed through a column of 70 g of silica gel (Wako Gel C-200), and the silica gel column was washed with 100 ml of toluene and then eluted with ethyl acetate-toluene (3:1) to give 306 mg of a colorless powder comprising 1,2′,6′-tri-N-tert-butoxycarbonyl-3-demethoxyistamycin $B_o$ 4,5-carbamate. Yield 93%.

(e) 1,2′,6′-Tri-N-tert-butoxycarbonyl-3-demethoxyistamycin $B_o$ 4,5-carbamate (293 mg, 0.466 milimoles) obtained in the above procedure (d) was dissolved in 10 ml of dioxane and the resultant solution was admixed with 5 ml of 0.2M aqueous barium hydroxide, followed by agitation at 100° C. overnight to effect the hydrolytic fission of the cyclic 4,5-carbamate ring of the istamycin $B_o$ compound. The reaction solution was neutralized by addition of gaseous carbon dioxide and filtered to remove the insoluble matter precipitated therefrom. The precipitate as filtered out was washed with dioxane and the washing was combined with the filtrate. The combined solution was concentrated under reduced pressure and the residue was purified by column chromatography on silica gel (Wako Gel C-200, 30 g) developed with chloroform-methanol-17% aqueous ammonia (80:10:1) to afford 255 mg of a colorless powder comprising 1,2′,6′-tri-N-tert-butoxycarbonyl-3-demethoxyistamycin $B_o$. Yield 90%. This product showed a decomposition point of 131°–135° C. and a specific optical rotation $[\alpha]_D^{20}$ +70° (c 0.3, chloroform).

(2) Synthesis of 3-demethoxyistamycin B (a) 1,2′,6′-Tri-N-tert-butoxycarbonyl-3-demethoxyistamycin $B_o$ (242 mg, 0.401 milimoles) obtained in the procedure of Example 1 (1)(e) as above was dissolved in 5 ml of dioxane, and the solution obtained was admixed with 0.1 ml of triethylamine and 164 mg (0.602 milimoles) of N-(N-tert-butoxycarbonylglycyloxy)succinimide (as an active ester of an N-protected glycine), followed by agitation at 60° C. overnight to effect the glycylation of the 4-methylamino group of the istamycin $B_o$ compound. The reaction solution was concentrated to dryness under reduced pressure and the solid residue was taken up into 10 ml of chloroform. The solution in chloroform was washed with 5% aqueous ammonia and with water, subsequently dried over anhydrous sodium sulfate and then concentrated to dryness to afford a crude powder of 1,2′,6′,2″-tetra-N-tert-butoxycarbonyl-3-demethoxyistamycin B.

(b) This crude powder was dissolved in 2.2 ml of 90% aqueous trifluoroacetic acid and the solution obtained was stirred at ambient temperature for 45 minutes to effect the hydrolytic removal of the amino-protecting tert-butoxycarbonyl groups.

The reaction solution was concentrated and the oily material obtained was washed with ethyl ether to give a powder. This powder was taken up into 10 ml of water and the aqueous solution was passed through a column of a cation-exchange resin, Amberlite CG-50 (20 ml, $NH_4^+$ form, a product of Rohm & Haas Co., U.S.A.). The resin column was then eluted gradiently with 60 ml portions of 0.1N, 0.2N, 0.4N, 0.6N and 0.7N aqueous solutions of ammonia. When the elution was made using the 0.6N aqueous ammonia, the active eluate was obtained and concentrated to dryness, affording 78 mg of 3-demethoxyistamycin B (dihydrate) as a colorless powder of a decomposition point of 201°–220° C. and $[\alpha]_D^{24}$ +89° (c 0.5, water). Yield 49%.

EXAMPLE 2

Synthesis of 3-demethoxy-2″-N-formimidoylistamycin B (a) 1,2′,6′-Tri-N-tert-butoxycarbonyl-3-demethoxyistamycin $B_o$ (730 mg, 1.21 milimoles) obtained in Example 1 (1)(e) as above was dissolved in 12 ml of dioxane, and the resultant solution was admixed with 0.15 ml of triethylamine and 742 mg (2.42 milimoles) of N-(N-benzyloxycarbonylglycycloxy)succinimide (as an active ester of an N-protected glycine). The admixture obtained was stirred at 60° C. overnight and the reaction solution was concentrated to dryness. The solid residue was taken up into 20 ml of chloroform and the solution in chloroform was washed with 5% auqeous ammonia and then with water, followed by drying over anhydrous sodium sulfate and concentrating to dryness. The residue was purified by column chromatography on silica gel (Wako Gel C-200, 50 g) developed with ethyl acetate-toluene (5:1) to give 468 mg of a colorless powder of 2″-N-benzyloxycarbonyl-1,2′,6′-tri-N-tert-butoxycarbonyl-3-demethoxyistamycin B. Yield 49%.

(b) 2″-N-Benzyloxycarbonyl-1,2′,6′-tri-N-tert-butoxycarbonyl-3-demethoxyistamycin B (450 mg, 0.567 milimoles) obtained in the above procedure (a) was dissolved in a mixture of 12 ml of methanol, 3 ml of water and 0.1 ml of acetic acid. The admixture obtained was subjected to hydrogenolysis in the presence of 5% palladium-on-carbon catalyst under a stream of hydrogen gas for 4 hours to effect the removal of the amino-protecting benzyloxycarbonyl group from the istamycin B compound. The reaction mixture was then filtered to remove the catalyst therefrom, and the filtrate was concentrated under reduced pressure. The residue was taken up into 30 ml of chloroform and the solution obtained was washed with 1N aqueous sodium hydroxide and then with water. The chloroform phase so washed was dried over anhydrous sodium sulfate and concentrated to dryness to afford 374 mg of 1,2',6'-tri-N-tert-butoxycarbonyl-3-demethoxyistamycin B. Yield 100%.

(c) 1,2',6'-Tri-N-tert-butoxycarbonyl-3-demethoxyistamycin B (364 mg, 0.551 milimoles) obtained in the above procedure (b) was dissolved in 10 ml of ethanol, to which was then added 250 mg (2.2 milimoles) of ethylformamide hydrochloride ($H_5C_2OCH=NH \cdot HCl$) at 0° C. under ice-cooling. The mixture obtained was agitated at ambient temperature overnight and the reaction solution was concentrated to dryness, followed by extracting the residue with ethyl acetate. The extract in ethyl acetate was filtered to remove the insoluble matter, and the filtrate was concentrated to dryness. The residue so obtained was purified by column chromatography on Sephadex LH-20 (a product of Pharmacia Co., Sweden, 100 ml) developed with a mixture of ethyl acetate-methanol (5:1) to afford 268 mg of 1,2',6'-tri-N-tert-butoxycarbonyl-3-demethoxy-2''-N-formimidoylistamycin B. This product was dissolved in 2 ml of 90% aqueous trifluoroacetic acid, followed by agitation at ambient temperature for 45 minutes to effect the hydrolytic removal of the amino-protecting tert-butoxycarbonyl groups therefrom. The reaction solution was concentrated under reduced pressure and the oily material obtained was washed with ethyl ether to give a powder comprising 3-demethoxy-2''-N-formimidoylistamycin B. This powder was taken up into 1 ml of water and the aqueous solution obtained was passed through a column of an anion-exchange resin, Amberlite IRA-400 (12 ml, $SO_4^{2-}$ form, a product of Rohm & Haas Co., U.S.A.). This resin column was then developed with water and the eluate was collected in 2 ml-fractions. Such fractions which were positive to ninhydrin were combined together and concentrated to dryness to obtain a crude powder of 3-demethoxy-2''-N-formimidoylistamycin B sulfate. This powder was purified by column chromatography on carbon (10 ml) developed with water, affording 112 mg of a colorless powder of 3-demethoxy-2''-N-formimidoylistamycin B (disulfate tetrahydrate). Yield 31%. This product showed a decomposition point of 201°-220° C. and a specific optical rotation $[\alpha]_D^{24} +89°$ (c 0.5, water).

REFERENCE EXAMPLE

Synthesis of 3-O-demethylistamycin $B_o$

Istamycin $B_o$ monocarbonate (500 mg, 1.27 mmol) was dissolved in 48% hydrobromic acid (50 ml) and the solution was heated in a sealed tube at 90°-93° C. for 4 hours. The reaction solution was concentrated to dryness in vacuo and the residue was dissolved in water (50 ml). The solution was adjusted to pH 8.5 with addition of 7M aqueous ammonia and passed through a column (21×550 mm) of 200 ml of CM-Sephadex C-25 ($NH_4$-form, a product of Pharmacia Co., Sweden). The column was eluted gradiently with 0.15M aqueous ammonia (1120 ml) and 0.70M aqueous ammonia (1120 ml). The eluate was collected in 16 ml-fractions. The fractions Nos. 85 to 102 were combined together and concentrated to dryness in vacuo to afford 275 mg of a colorless powder of 3-O-dimethylistamycin $B_o$ dicarbonate. Yield 49%.

What we claim is:

1. A compound of the formula

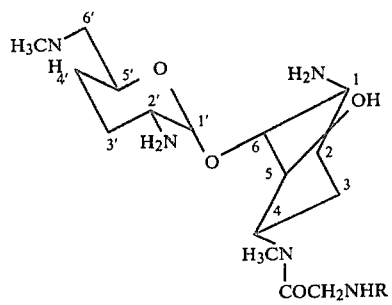

wherein R is selected from the group consisting of a hydrogen atom and a formimidoyl group, or a pharmaceutically acceptable acid addition salt thereof.

2. The compound of claim 1 which is 3-demethoxyistamycin B or a pharmaceutically acceptable acid addition salt thereof.

3. The compound of claim 1 which is 3 demethoxy-2''-N-formimidoylistamycin B or a pharmaceutically acceptable acid addition salt thereof.

4. A process for the production of 3-demethoxyistamycin B as claimed in claim 1, which comprises the consecutive steps of:

(a) removing the 3-hydroxyl group from a compound of the formula (VI)

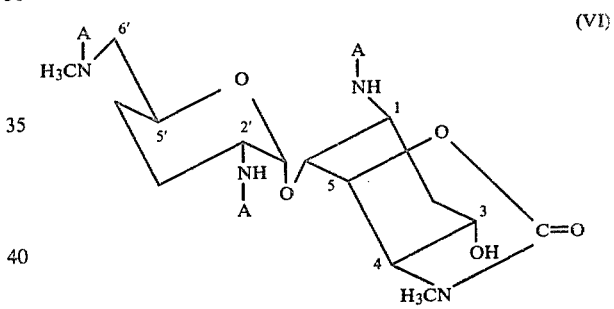

by reacting the compound (VI) with sulfuryl chloride ($SO_2Cl_2$) in dry pyridine at a temperature of not higher than 0° C. to produce the corresponding 1,2',6'-tri-N-protected 3-demethoxy-3-epi-chloroistamycin $B_o$ 4,5-carbamate, and then by reducing the latter 3-epi-chloro compound with a trialkyltin hydride in the presence of α,α-azobisisobutyronitrile, to produce a 1,2',6'-tri-N-protected 3-demethoxyistamycin $B_o$ 4,5-carbamate derivative of the formula (VII)

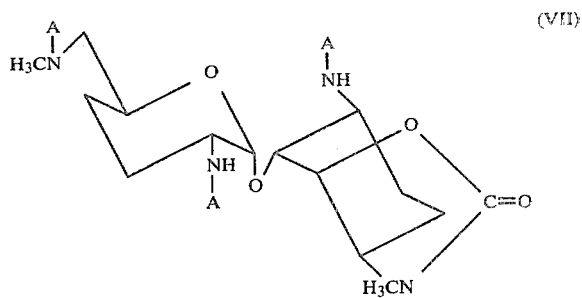

wherein A is as defined above, (b) fissioning the cyclic 4,5-carbamate moiety of the compound of the formula (VII) by alkaline hydrolysis to produce a 1,2',6'-tri-N-protected 3-demethoxyistamycin B₀ derivative of the formula (III)

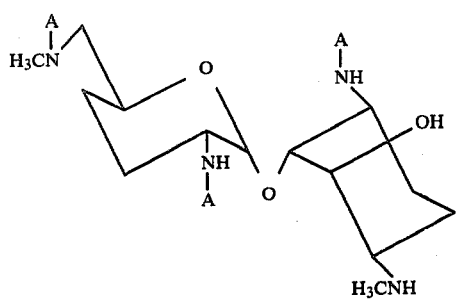
(III)

wherein A is as defined as above, (c) acylating the 4-methylamino group of the compound of the formula (III) with glycine or an N-protected glycine derivative of the formula (IV)

 (IV)

wherein B is a hydrogen atom or an amino-protecting group, to produce a 1,2',6'-tri-N-protected or 1,2',6',2"-tetra-N-protected 3-demethoxyistamycin B derivative of the formula (V)

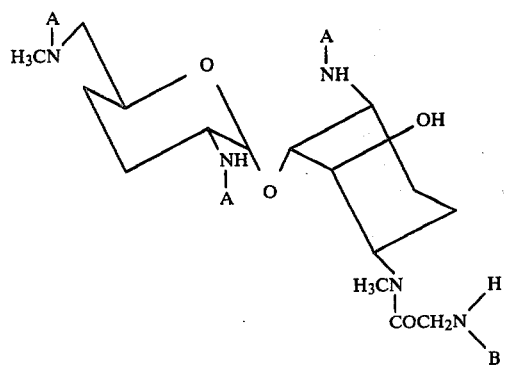
(V)

wherein A and B are as defined above, and (d) removing all the remaining amino-protecting groups (A and B) from the compound of the formula (V) to give the desired 3-demethoxyistamycin B.

5. A process as claimed in claim 4 in which the acylation of the 4-methylamino group of the compound of the formula (III) is effected using an active ester of an N-protected glycine.

6. A process for the production of 3-demethoxy-2"-N-formimidoylistamycin B as claimed in claim 1, which comprises the consecutive steps of:

(a) removing the 3-hydroxyl group from a compound of the formula (VI)

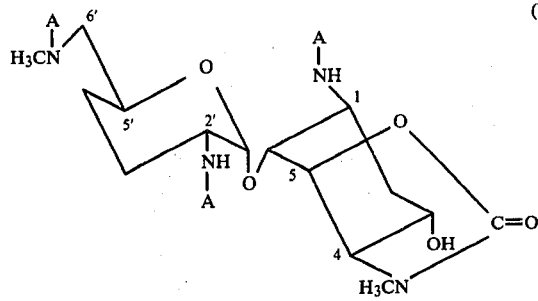
(VI)

by reacting the compound (VI) with sulfuryl chloride in dry pyridine at a temperature of not higher than 0° C. to produce the corresponding 1,2',6'-tri-N-protected 3-demethoxy-3-epi-chloroistamycin B₀ 4,5-carbamate, and then by reducing the latter 3-epi-chloro compound with a trialkyltin hydride in the presence of α,α-azobisisobutyronitrile, to produce a 1,2',6'-tri-N-protected 3-demethoxyistamycin B₀ 4,5-carbamate derivative of the formula (VII)

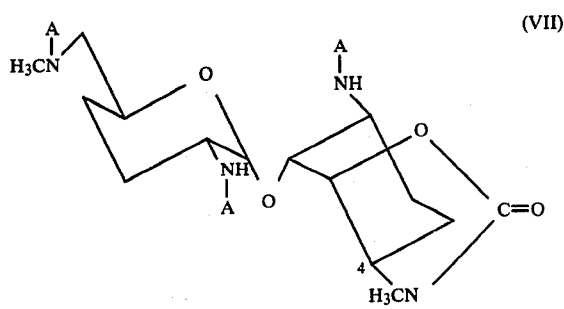
(VII)

wherein A is as defined above, (b) fissioning the cyclic 4,5-carbamate moiety of the compound of the formula (VII) by alkaline hydrolysis to produce a 1,2',6'-tri-N-protected 3-demethoxyistamycin B₀ derivative of the formula (III)

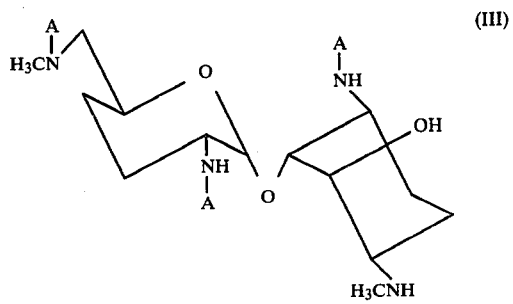
(III)

wherein A is a defined above, (c) acylating the 4-methylamino group of the compound of the formula (III) with glycine or an N-protected glycine derivative of the formula (IV')

 (IV')

wherein B' is a hydrogen atom or an amino-protecting group, to produce a 1,2',6'-tri-N-protected or 1,2',6',2"-tetra-N-protected 3-demethoxyistamycin B derivative of the formula (V')

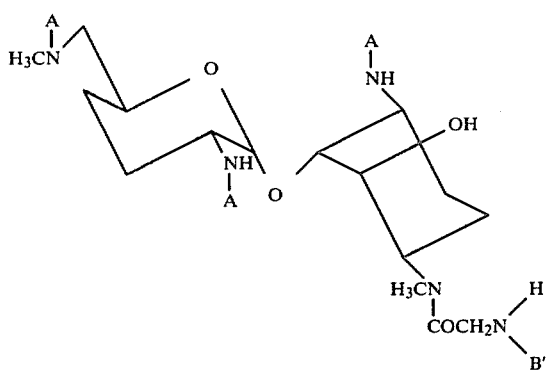

(V')

(d) removing the amino-protecting group (B') from the 2"-amino group of the compound of the formula (V') where B' denotes the amino-protecting group, to produce the 1,2',6'-tri-N-protected 3-demethoxyistamycin B derivative of the formula (V")

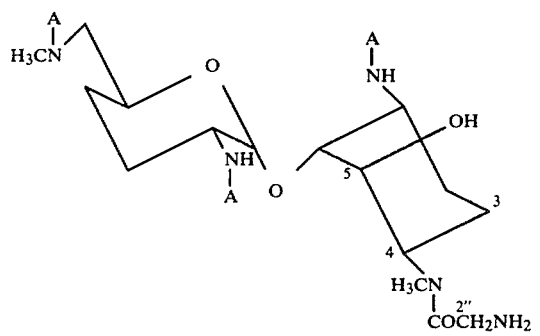

(V")

wherein A is as defined above, (e) reacting the 2"-amino group of the compound of the formula (V") with an iminoether of the formula (VIII)

R"OCH=NH    (VIII)

wherein R" is a ($C_1$–$C_4$) alkyl group or an aralkyl group, or an acid addition salt of said iminoether to produce a 1,2',6'-tri-N-protected 3-demethoxy-2"-N-formimidoylistamycin B derivative of the formula (Ib')

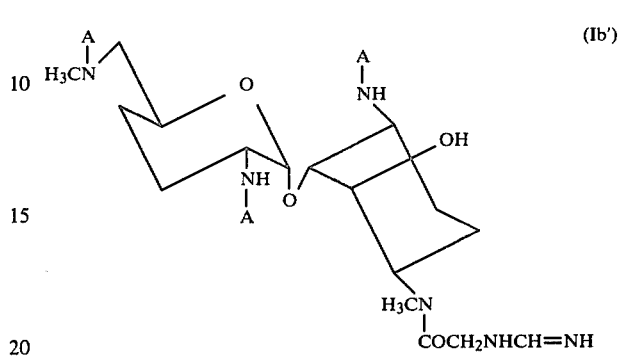

(Ib')

wherein A is a defined above, and (f) removing all the remaining amino-protecting groups (A) from the compound of the formula (Ib') to give the desired 3-demethoxy-2"-N-formimidoylistamycin B.

7. A process as claimed in claim 6 in which the acylation of the 4-methylamino group of the compound of the formula (III) is effected using an active ester of an N-protected glycine.

8. A pharmaceutical composition comprising as the active ingredient a compound of the formula (I) as defined in claim 1 or a pharmaceutically acceptable acid addition salt thereof in an antibacterially effective amount, in combination with a pharmaceutically acceptable carrier or adjuvant.

9. The compound, 1,2',6'-Tri-N-tert-butoxycarbonylistamycin $B_o$ 4,5-carbamate.

10. The compound, 1,2',6'-tri-N-tert-butoxycarbonyl-3-demethoxyistamycin $B_o$ 4,5-carbamate.

11. The compound, 1,2',6'-tri-N-tert-butoxycarbonyl-3-demethoxyistamycin $B_o$.

12. A compound, 1,2',6'-tri-N-tert-butoxycarbonyl-3-demethoxy-3-epi-chloroistamycin $B_o$ 4,5-carbamate.

* * * * *